(12) United States Patent
Sahib et al.

(10) Patent No.: US 11,712,410 B2
(45) Date of Patent: *Aug. 1, 2023

(54) COMPOSITION FOR IMPROVING HAIR HEALTH

(71) Applicant: K18, Inc., San Francisco, CA (US)

(72) Inventors: Suveen Sahib, Novato, CA (US); Elsa Jungman, San Francisco, CA (US)

(73) Assignee: K18, INC., San Francisco, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 16/122,796

(22) Filed: Sep. 5, 2018

(65) Prior Publication Data

US 2020/0069551 A1 Mar. 5, 2020

(51) Int. Cl.
| | | |
|---|---|---|
| *A61K 8/65* | (2006.01) | |
| *A61P 17/14* | (2006.01) | |
| *A61K 8/44* | (2006.01) | |
| *A61K 8/49* | (2006.01) | |
| *A61K 38/17* | (2006.01) | |
| *A61Q 5/02* | (2006.01) | |
| *A61Q 5/10* | (2006.01) | |
| *A61Q 5/12* | (2006.01) | |
| *C07K 7/06* | (2006.01) | |
| *C07K 7/08* | (2006.01) | |

(52) U.S. Cl.
CPC ............... *A61K 8/65* (2013.01); *A61K 8/44* (2013.01); *A61K 8/492* (2013.01); *A61K 38/1748* (2013.01); *A61P 17/14* (2018.01); *A61Q 5/02* (2013.01); *A61Q 5/10* (2013.01); *A61Q 5/12* (2013.01); *C07K 7/06* (2013.01); *C07K 7/08* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 5,028,419 A | 7/1991 | Pigiet | |
| 5,635,170 A | 6/1997 | Lang et al. | |
| 10,709,655 B2 | 7/2020 | Cavaco et al. | |
| 2006/0272103 A1 | 12/2006 | Barbarat | |
| 2006/0286655 A1 | 12/2006 | Philippe | |
| 2010/0272666 A1 | 10/2010 | Breakspear et al. | |
| 2016/0271043 A1* | 9/2016 | Cavaco Paulo | A61Q 5/04 |
| 2019/0307666 A1 | 10/2019 | Cavaco Paulo et al. | |

FOREIGN PATENT DOCUMENTS

| | | | |
|---|---|---|---|
| CN | 103126949 A * | 6/2013 | |
| EP | 0488242 A1 | 6/1992 | |
| EP | 04882421 | 6/1992 | |
| EP | 1705188 A1 | 9/2006 | |
| FR | 2706300 A1 | 12/1994 | |
| FR | 2876286 A1 | 4/2006 | |
| GB | 103484 A | 1/1918 | |
| JP | H0656889 A | 3/1994 | |
| JP | 2005151849 A | 6/2005 | |
| PT | 103484 A | 11/2007 | |
| WO | 1997011672 | 4/1997 | |
| WO | WO1997011672 A1 | 4/1997 | |
| WO | 2000023039 | 4/2000 | |
| WO | WO2000023039 A2 | 4/2000 | |
| WO | 2000051556 | 9/2000 | |
| WO | WO2000051556 | 9/2000 | |
| WO | 2000064405 | 11/2000 | |
| WO | WO2000064405 A2 | 11/2000 | |
| WO | WO-2004048399 A2 | 6/2004 | |
| WO | WO-2005049834 A1 | 6/2005 | |
| WO | 2006001536 | 1/2006 | |
| WO | WO2006001536 A1 | 1/2006 | |
| WO | WO-2007136286 A1 | 11/2007 | |
| WO | 2008081348 | 7/2008 | |
| WO | WO2008081348 A2 | 7/2008 | |
| WO | WO-2010010145 A1 | 1/2010 | |
| WO | WO-2011072991 A1 | 6/2011 | |
| WO | 2012013593 | 2/2012 | |
| WO | WO2012013593 A1 | 2/2012 | |
| WO | 2015056216 | 4/2015 | |
| WO | WO2015056216 A2 | 4/2015 | |
| WO | WO-2015056216 A2 * | 4/2015 | ............. A61K 8/645 |

OTHER PUBLICATIONS

BLAST glossary downloaded from www.ncbi.nlm.nih.gov on May 2, 2020 (Year: 2020).*
"Chapter 2 Evolutionary Concept in Genetics and Genomics" in Koonin EV, Galperin MY. Sequence—Evolution—Function: Computational Approaches in Comparative Genomics. Boston: Kluwer Academic; 2003. Available from: https://www.ncbi.nlm.nih.gov/books/NBK20260/ (Year: 2003).*
Fernanda Reis Gavazzoni Dias "Hair Cosmetics: An Overview," International Journal of Trichology, Jan.-Mar. 2015, vol. 7, pp. 2-15 (Year: 2015).*
Romanowski "An introduction to cosmetic technology," American Oil Chemists' Society, 2020 (Year: 2020).*
BLAST search for SEQ ID No. 1, downloaded May 2, 2020 (Year: 2020).*
BLAST search for SEQ ID No. 2, downloaded May 2, 2020 (Year: 2020).*

(Continued)

*Primary Examiner* — Christina Bradley
(74) *Attorney, Agent, or Firm* — Wilson Sonsini Goodrich & Rosati

(57) ABSTRACT

A composition comprising two peptides with a size of 11 and 12 amino acids, wherein 2-3 of said amino acids are cysteines and a suitable dermatology excipient, which can be used for treatment and grooming products for animal hair, preferably for treatment and cosmetics for human hair.

7 Claims, 2 Drawing Sheets

Specification includes a Sequence Listing.

(56) References Cited

OTHER PUBLICATIONS

U.S. Forest Service entry on soaps at www.fs.fed.us/wildflowers/ethnobotany/soaps.shtml, downloaded Sep. 29, 2020 (Year: 2020).*
Yang, "Chapter 36: Hair Care Cosmetics," Cosmetic Science and Technology: Theoretical Principles and Applications, 2017 (Year: 2017).*
Fernandes;.Lima; Loureiro, Gomes & Cavco-Paulo, 2012, "Keratin-based peptide: Biological evaluation and strengthening properties on relaxed hair," International Journal of Cosmetic Science, 2012, 34, 338-346.
Co-pending U.S. Appl. No. 18/164,515, inventors Sahib; Suveen [Us] et al., filed Feb. 3, 2023.
Co-pending U.S. Appl. No. 18/194,372, inventors Cavaco Paulo; Arthur Manuel et al., filed Mar. 31, 2023.
Dow, Carbowax Sentry Polyethylene Glycols, published online 2011.
Fernandes et al. Keratin-based peptide: biological evaluation and strengthening properties on relaxed hair. International journal of cosmetic science 34(4):338-346 (2012).
Marabotti et al. The misuse of terms in scientific literature. Bioinformatics 26(19):2498 (2010).
Naturally Curly, http://www.naturallycurly.com/curlreading/kinky-hair-type-4a/ingredients-commonly-used-in-hair-care-productspeg-modified-materials/, published online Jun. 8, 2010.
PCT/IB2014/065375 International Search Report and Written Opinion dated Jun. 7, 2015.
Shimomura et al. Human Hair Keratin-Associated Proteins. J Investig Dermatol Symp Proc 10:230-233 (2005).
Thesis from Celia Freitas Da Cruz, Unraveling and modulating human hair morphology features (192 pgs) (2012).
Uniprot Protein Database, protein accession A8MUX0, Keratin-associated protein 16-1, accessed on Dec. 18, 2019.
Uniprot Protein Database, protein accession P26371, Keratin-associated protein 5-9, accessed on Dec. 18, 2019.
Uniprot Protein Database, protein accession Q9NSB0, Type II hair keratin 6, accessed on Dec. 18, 2019.
Uniprot Protein Database, protein Accession Q9NSB5, accessed on Nov. 8, 2019.
Uniprot protein database, protein Type II hair keratin 1, protein accession Q9NSB5, accessed on Aug. 28, 2017.
U.S. Appl. No. 15/030,313 Office Action dated Aug. 29, 2018.
U.S. Appl. No. 15/030,313 Office Action dated Aug. 31, 2017.
U.S. Appl. No. 15/030,313 Office Action dated Jan. 11, 2019.
U.S. Appl. No. 15/030,313 Office Action dated Jan. 24, 2018.
U.S. Appl. No. 15/030,313 Office Action dated Jul. 18, 2019.
U.S. Appl. No. 15/030,313 Office Action dated Mar. 2, 2017.
U.S. Appl. No. 16/439,889 Office Action dated Apr. 1, 2022.
U.S. Appl. No. 16/439,889 Office Action dated Jan. 3, 2020.
U.S. Appl. No. 16/439,889 Office Action dated Sep. 15, 2022.

* cited by examiner

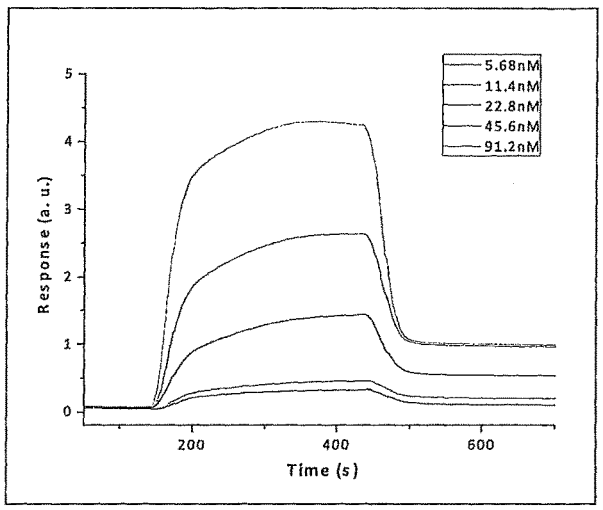
FIG 1: Evaluation of the binding affinity of Keratin to peptide Aquis 1 (FCGFPSCSTSG). The equilibrium dissociation constant (KD Value) was $3.65.10^{-7}$ M. (Ka= $1.31.10^3$ $M^{-1.s-1}$, Kd=$4.78.10^{-4s-1}$)
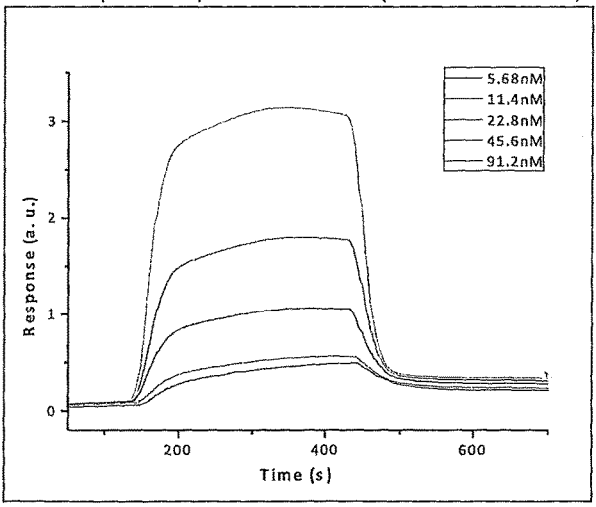
FIG 2: Evaluation of the binding affinity of Keratin to peptide 2 (CTPPSCCQLHHA). The equilibrium dissociation constant (KD Value) was $2.50.10^{-6}$ M. (Ka= $8.24.10^3$ $M^{-1.s-1}$, Kd=$2.06.10^{-2s-1}$)

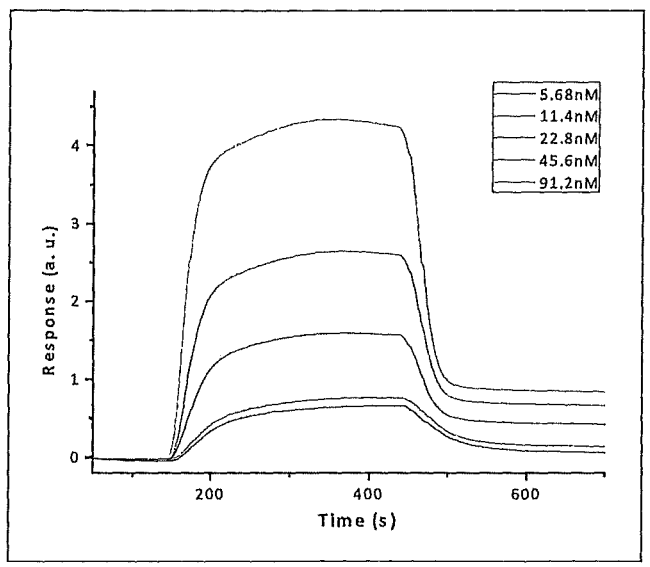
FIG 3: Evaluation of the binding affinity of Keratin to peptide 3 (GGVCGPSPPCITT). The equilibrium dissociation constant (KD Value) was $8.14 \cdot 10^{-7}$ M. ($Ka= 8.50 \cdot 10^3$ $M^{-1}s^{-1}$, $Kd=6.92 \cdot 10^{-3 s^{-1}}$)

SEQUENCE LISTING

<160> NUMBER OF SEQ ID NOS: 4

<210> SEQ ID NO 1
<211> LENGTH: 11
<212> TYPE: PRT
<213> ORGANISM: Artificial Sequence
<220> FEATURE:
<223> OTHER INFORMATION: PEPTIDE

<400> SEQUENCE: 1

Phe Cys Gly Phe Pro Ser Cys Ser Thr Ser Gly
1               5                   10

<210> SEQ ID NO 2
<211> LENGTH: 12
<212> TYPE: PRT
<213> ORGANISM: Artificial Sequence
<220> FEATURE:
<223> OTHER INFORMATION: PEPTIDE

<400> SEQUENCE: 2

Cys Thr Pro Pro Ser Cys Cys Gln Leu His His Ala
1               5                   10

<210> SEQ ID NO 3
<211> LENGTH: 10
<212> TYPE: PRT
<213> ORGANISM: Artificial Sequence
<220> FEATURE:
<223> OTHER INFORMATION: PEPTIDE

<400> SEQUENCE: 3

Ala Ser Cys Cys Arg Pro Ser Tyr Cys Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: PEPTIDE
<220> FEATURE:
<221> NAME/KEY: MOD_RES
<222> LOCATION: (1)..(1)
<223> OTHER INFORMATION: PALMITOYL IS ATTACHED TO THIS POSITION

<400> SEQUENCE: 4

Ala Ser Cys Cys Arg Pro Ser Tyr Cys Gly
1               5                   10

COMPOSITION FOR IMPROVING HAIR HEALTH

TECHNICAL FIELD

The present application relates to compositions comprising for use in treatment and cosmetics for animal, preferably human hair.

BACKGROUND OF THE INVENTION

The hair has a significant social role in most of the various world cultures, especially for the female population. Thus, there is a constant desire to improve and change the hair characteristics, such as its natural texture.

There are several differences in hair characteristics among different races of mankind, as well as between individuals of the same race, such as length, thickness, color and texture.

Hair is composed of approximately 65% to 95% protein. The remaining constituents include water, lipids, pigments and trace elements. Most of the proteins that make up hair corresponds to keratin and keratin-associated proteins.

The structure of human hair fibers consists of the cuticle, cortex and medulla. The cuticle consists of overlapping layers of cells, similar to a system of scales, which comprises high content of cysteine and providing a protective character to the hair fiber. It constitutes about 15% of the hair weight. The hair cortex is the intermediate region, is responsible for the strength, elasticity and hair color. It consists of many cell types and represents about 80% of the hair weight. The cord corresponds to a central beam cells do not exist in all types of hair.

The keratins and especially keratin-associated proteins have high sulfur content which is present in the amino acid cysteine. The presence of sulfur is essential for hair structure, since it allows the formation of disulfide bonds between polypeptide chain of amino acids, due to oxidation of cysteine residues. The existence of these bonds is largely responsible for the structure and hair texture.

There are several methods available to style the hair involving breaking and restoration of new disulfide bridges, allowing relaxation and straightening hair. However, the methods currently alter more effectively use harmful chemicals such as sodium hydroxide, potassium hydroxide, lithium hydroxide, guanidine hydroxide, ammonium thioglycolate or sodium sulfate. These methods can damage the scalp and the hair fiber cuticle in both the cortex and leading to its weakening and lowering its tensile strength. Formaldehyde is also used in products for hair straightening, being, however, extremely toxic. Other hair treatments that do not involve as much damage to the hair and the consumer are usually very expensive and time-consuming or low effectiveness. Thus there is a constant demand for formulations to model efficiently without damaging the hair fiber.

As indicated above, hair is a complex structure and is comprised of thin, overlapping cuticle cells that protect its inner core, known as the cortex. The cuticle cells are mechanically tough and very resistant to environmental insults, and to the penetration of foreign molecules, due to the high degree of isodipeptide and disulfide bonds present in its various lamellar layers. The cortex, which constitutes most of the fiber mass, contains spindle-shaped cortical cells filled with macrofibrils (higher ordered structures of alpha-keratin proteins embedded in an amorphous protein matrix (primarily comprised of keratin associated proteins). A cell membrane complex joins cuticle cells with other cuticle cells, cortical cells with other cortical cells, and cuticle and cortical cells.

Treating hair with peptides presents two challenges. The first is the successful penetration of the peptide into the hair cortex. This is not an easy endeavor, especially in virgin, undamaged hair. It should be noted that molecular size and polarity play a large role in determining the ability of a molecule to gain access to the interior of the fiber structure. Also, damaged hair is more permeable than undamaged hair. More than likely this is due to the increased porosity of damaged hair, especially hair that has undergone chemical treatments. 2) Once penetration has been achieved, the second challenge is understanding how the peptides influence the physicochemical properties of the fiber. We now have several studies demonstrating the ability of low molecular weight peptides to gain access to the cortex of damaged hair and increase its mechanical properties. 3-6 Improving mechanical strength is highly desirable in hair that has undergone chemical or thermo-mechanical treatments in which case its structural integrity becomes compromised.

Peptides, proteins, and amino acid derivatives have also been used in compositions for personal care products in particular hair for its conditioning and strengthening. For example, WO2000023039A2 discloses a composition for hair treatment containing intermediate filament proteins, particularly keratin artificial. EP 0488242 discloses an agent for hair treatment containing 3% to 10% amino acid weight cysteine or salts thereof and a saccharide or polyhydric alcohol containing four to twenty carbon atoms, three or more hydroxyl groups in the molecule and any aldehyde or ketone group. WO2015056216A2 used peptides with a size of 6-12 amino acids, wherein 2-5 of said amino acids are cysteines, which can be used for cosmetics treatments for human hair. This patent show that these small peptides can penetrate the hair and improve mechanical resistance from within by interacting with hair keratin.

WO 00/51556 discloses a hair treatment composition that contains four or more discrete molecules of different amino acids selected from histidine, lysine, methionine, tyrosine, tryptophan or cysteine. This document describes peptides without reference sequence and a composition based essentially on histidine, lysine, methionine, tyrosine, tryptophan or cysteine.

The GB 103 484 discloses a formulation for cosmetic applications which utilize hydrophobic binding domains and/or carbohydrates, in order to enhance its properties and to repair hair damage and have been used as binding domain milk protein hydrolyzate, a model of human surfactant protein as well as biologically active and some synthetic peptides. The present invention is distinguished by the innovative use of analogous synthetic peptide sequences to keratin proteins instead of surface active proteins of the lung or is based on hydrophobic binding domains and/or carbohydrates, but in other types of interactions, namely disulfide bridges.

Enzymes have also been used as activating agents for hair treatments, such as in WO2012013593A1 discloses a cosmetic kit for conformational changes that specifically acts hair keratin in hair, especially in disulfide bonds, wherein the formulation has enzyme activating agents and proteolytic enzymes.

As described earlier in the document's hair treatments involving performances in terms of disulfide bonds of the hair, of which we highlight a few.

WO1997011672A1 describes a permanent hair processing method that uses phosphine tris (2-carboxyethyl) (TCEP) and other water soluble tertiary phosphines to break the disulfide bonds, whose reaction takes place in an acidic medium. U.S. Pat. No. 5,635,170 discloses a composition for permanent shaping of hair based WO2000064405A2 on a keratin reducing agent which contains N-glycyl-L-cysteine and/or L-cysteinyl-glycine. This composition is in the range of pH of 6.5 to 9.0. WO2008081348A2 discloses a method and composition for permanent hair shaping, by use of 1% to 30% N-alkyl-2-mercaptoacetamide as a keratin reducing and at least one cationic surfactant for permanently shaping hair and the resulting process. WO2006001536A1 describes an agent for permanent hair processing containing a mercaptocarboxylic acid derivative, which allows processing and reduction of hair keratin in a pH region of neutral to acidic. US20100272666A1 discloses a hair cosmetic composition for hair treatment, wherein the number of amino acids of the peptide is 5 to 50, but contains no cysteine residues and amino acid derivative. Thus, this invention is distinguished by the existence of specific amino acid sequences containing cysteine, allowing the formation of disulfide bonds which stabilize and protect the hair fiber.

In a previous article Fernandes et al. (Fernandes Lima, Laurel, Gomes, Paulo & Babble-2012) is made toxicological assessment of a peptide sequence with treatments for hair not described containing 13 amino acids with two cysteines in its composition. In this article it is not mentioned or suggested that the percentage of cysteine in a peptide sequence may have some effect on hair strength, and that the present innovation the number of amino acids in each peptide sequence is 6 to 12.

A recent study by researchers at the University of Minho in March 2017 (PhD Thesis from Celia Freitas Da Cruz, Unravelling and modulating human hair morphology features) brought to light a mechanistic understanding of how peptides could interact and fortify endogenous hair proteins. In their investigations, they examined the influence of isoelectric point, charge, and amino acid side chain functionality on the binding interactions of the screened peptides with hair proteins. The array analysis suggested that designing peptides with small molecular weights and high affinity to human hair keratin would have a good probability to interact and reinforce keratin properties when supported by surfactant agents that can help increase the penetration of peptides into the cortex.

SUMMARY OF THE INVENTION

Accordingly the present invention is a peptide composition for treating hair, comprising: at least one peptide having an 11-12 amino acid size, the full size of the peptide sequence, including 2-3 cysteine amino acids; and at least one excipient suitable for dermatology use.

BRIEF DESCRIPTION OF THE DRAWINGS

FIG. 1 is a graph showing the binding affinity of keratin to Aquis peptide 1.
FIG. 2 is a graph showing the binding affinity of keratin to Aquis peptide 2.
FIG. 3 is a graph showing the binding affinity of keratin to Aquis peptide 3.

BEST MODE FOR CARRYING OUT THE INVENTION

The present invention is distinguished by the use of peptides that can penetrate inside the human hair fiber to improve its strength and hydrophobicity and have more affinity to hair keratin compared to previously developed peptides.

The present invention is directed to novel peptide designs having the following characteristics:
1. Low molecular weight to penetrate the core of the hair strand
2. Affinity and ability to interact with keratin
3. Hydrophobic
4. Works from the inside out to protect hair from water damage.

The sequence includes the following characteristics:
1. Contain a Cysteine—which will naturally form disulfide bonds with other free cysteine in the hair/keratins
2. Contain some hydrophobic residues and/or fatty acid labels for added hydrophobicity
3. Will be a length of 540 amino acids in length, to keep MW low with some Polar and/or Basic amino acids Based on analysis of the Keratin-associated protein 1-1 (KRTAP1-1). Given the different parameters, we wanted to ensure they incorporate all the best traits, including multiple cysteines which will bind to the free Keratins in the natural human hair. At first we thought a single cysteine would be good, but the evidence seems to indicate that multiple cysteines in a sequence, without disulfide bonds, may be the best, as they are then free to interact with the other free cysteines naturally occurring in the hair/keratins. They should all be 1042 amino acids long. We were also looking deeper to see if one sequence should be tested with a Palmitoyl on the N-terminus, which may be further beneficial with scalp skin uptake of the peptide, although it's not necessarily needed due to the use of other hydrophobic residues. What it allows is for a less hydrophobic peptide sequence to be used, and still offer the same properties but easier to synthesize.

The following sequences have been designed in this invention:

| | | |
|---|---|---|
| 1. ASCCRPSYCG (N-term) | | SEQ ID No. 4 |
| 2. FCGFPSCSTSG (non-repetitive domain) | | SEQ ID No. 1 |
| 3. CTPPSCCQLHHA (repetitive II domain) | | SEQ ID No. 2 |
| 4. Palmitoyl-ASCCRPSYCG (Pal N-term) | | SEQ ID No. 4 |

For the 4th one above a Palmitoyl group is added to the N-terminus to increase the hydrophobicity.

The Palmiotyl group on the N-terminus would be beneficial for the peptide to get into the scalp and follicle for improved protection (not growth), while the others are designed to bind to the external hair itself to provide the hydration and protection desired for a haircare product.

Carrying out the invention involves the following: Synthesize the sequences, and then see if any of them are overly difficult due to the extreme hydrophobic or multiple cysteine content. Also which sequences are more difficult and which ones will lend themselves better to larger, commercialization production scales.

Thus, the present invention aims to provide a composition for the treatment of the animal, including human hair, without the use of harmful chemicals to the hair fiber and consumer health in general and does not present the drawbacks found in the art.

The compositions described in this invention provide prolonged use hair with smooth texture, glossy, undamaged and with the desired characteristics and stronger. The peptide compositions with a number of specific amino acids and cysteine, act synergistically giving strength, toughness and elasticity to the hair. Thus, the compositions of the present invention are particularly relevant for treating the hair, coloring, permanent, etc.

The present application describes two peptides composition for the treatment or hair, in particular human or animal, comprising 11-12 amino acid size, wherein 2-3 of these cysteines are amino acids, dermatologically suitable excipients which penetrates the hair/by, increasing hair/resistance by decreasing and the hair breaks/by.

In one embodiment, improved results for the peptide (or peptides) of the peptide to the hair treatment composition may comprise between 11-12 amino acids, with the following sequences:

TABLE 1

| Sequence | Name AA |
|---|---|
| FCGFPSCSTSG<br>SEQ ID NO 1<br>LENGTH: 11<br>TYPE: PRT<br>ORGANISM: Artificial Sequence<br>FEATURE:<br>OTHER INFORMATION: PEPTIDE<br>SEQUENCE: 1<br>Phe Cys Gly Phe Pro Ser Cys Ser Thr Ser Gly<br>1               5                   10 | Aquis Pep1 |
| CTPPSCCQLHHA<br>SEQ ID NO 2<br>LENGTH: 12<br>TYPE: PRT<br>ORGANISM: Artificial Sequence<br>FEATURE:<br>OTHER INFORMATION: PEPTIDE<br>SEQUENCE: 2<br>Cys Thr Pro Pro Ser Cys Cys Gln Leu His His Ala<br>1               5                   10 | Aquis Pep 2 |

In yet another embodiment, the amount of cysteine of the peptide composition for hair treatment can range from 18% to 25% of the total amino acids of the peptide sequence In one embodiment, improved results for the peptide (or peptides) of the peptide to the hair treatment composition may comprise at least one sequence the following list having a degree of homology greater than or equal to 90%: Aquis Pep1 and Aquis Pep2, preferably with a degree of homology greater than or equal to 91%, 92%, 93%, 94%, 95%, 96%, 97%, 98%, 99%, 100%, In one embodiment, the peptide concentration of peptide composition for hair treatment can vary between 0.001% to 20% (w/w), preferably 0.01-5% (W/W).

In another embodiment, the peptide composition for hair treatment may further comprise at least one selected carrier in the following list: surfactants, emulsifiers, preservatives, thickeners, organic polymers, humectants, silicones, oils, fragrances, vitamins, buffers.

In yet another embodiment, the peptide composition for hair treatment may comprise at least one anionic surfactant selected from the following list: alkyl benzene sulfonates, ammonium lauryl sulfate, ammonium xylene sulfonate, sodium C14-16 olefin sulfonate, cocoyl sarcosinate sodium, sodium laureth sulfate, sodium lauryl sulfate, sodium lauryl sulfoacetate, sodium myreth sulfate, xylene sulfonate, sodium dodecylbenzene sulfonate, TEA, ethyl PEG-15 cocamine sulfate, dioctylsulfosuccinate and sodium) or mixtures thereof.

In one embodiment, the peptide composition for hair treatment may comprise at least one selected amphoteric surfactant from the following list: cocamidopropyl betaine, coca betaine, cocamphoacetate, cocanfodipropionato, disodium cocamphodiacetate, lauro ampho acetate cocoyl isethionate sodium or mixtures thereof.

In another embodiment, the peptide composition for hair treatment may comprise at least one cationic surfactant selected from the following list: quaternary ammonium compounds, berrentrimónio chloride, methosulfate berrentrimónio, benzalkonium chloride, cetrimonium chloride, cinamidopropiltrimónio, cocotrimonium chloride, dicetildimónio chloride, dicocodimónio chloride, dihydrogen tallow dimethyl ammonium chloride, hydrogenated triethylammonium chloride, dodecyl chloride (trimethyl) ammonium chloride, Quaternium-15 bentonite Quaternium-18, hectonita of Quaternium-22 dimetilbenziloctadecilamónio of chloride, tallow trimonium chloride, tricetildimónio chloride, or mixtures thereof.

In yet another embodiment, the peptide composition for hair treatment may comprise at least one nonionic surfactant selected from the following list: decyl glucoside, laureth-10, laureth-23, laureth-4, PEG-10 laurate sorbitan, polysorbate (20, 21, 40, 60, 61, 65, 80, 81), PPG-1-6 tridecete, sorbitol, estearato-(2, 10, 15, 20) CII-21 Pareth-(number between 3 and 30), PEG-20 C12 8 acid ester, or mixtures thereof.

In one embodiment, the peptide composition for hair treatment may comprise at least one emulsifier selected from the following list: succinate caprylic, capric, digliceril CIO 15 Pareth-(2,4,6,8), phosphate, -16 C14 glycol palmitate, glycol C18-20 isostearate, Ceteareth-(4-60), cocamidopropyl lauryl ether, Deceth-(3-10) DIPA-hydrogenated cocoate, dipentaeritritil hydroxystearate, dipentaeritritil hidroxisoestearato, dipentaeritritil hexacaprato/caprylate, dodoxinol-(5, 6, 7, 9, 12), nonoxynol (1-35) octoxinol-(1-70) octildodeceth-(2, 5, 16, 20, 25) Palm Kernel glycerides, or mixtures thereof.

In another embodiment, the peptide composition for hair treatment may comprise at least one selected preservative from the following list: butylparaben, diazolidinyl urea, hydantoin DMDM, ethylparaben, imidazolidinyl urea, iodopropynyl butylcarbamate, isobutylparaben, methylparaben, methylchloroisothiazolinone, phenoxyethanol, propylparaben, sodium benzoate, or mixtures thereof.

In yet another embodiment the peptide composition for hair treatment may comprise at least one thickener selected from the following list: stearate, ISOSTEARATE, myristate, laurate, aluminum palmitate, glycol distearate, hydrogenated castor oil, hydroxystearate oil hydrogenated castor oil, castor oil didrogenado isostearate, hydrogenated castor oil stearate, PEG-8 hydrogenated castor esters, PEG-150 distearate, or mixtures thereof.

In one embodiment, the peptide composition for hair treatment may comprise at least one naturally selected polymer derived from the following list: carboxymethyl hydroxyethyl cellulose, carboxymethyl hydroxypropyl guar, cellulose, ethyl cellulose, hydroxybutyl methyl cellulose, hydroxyethylcellulose, hydroxymethylcellulose, laurilpoliglicose, or its mixtures.

In another embodiment, the peptide composition for hair treatment may comprise at least one naturally derived humectant selected from the following list: 1,2,6 hexanetriol, dipropylene glycol, glycerin, hexylene glycol, panthenol, fitantriol, propylene glycol, sodium PCA, sorbitol, triethylene glycol, sorbitol dioleate, glucose, fructose, polydextrose, PCA potassium, hydrogenated honey, hyaluronic acid, inositol, wax hexanediol bee wax, hexanetriol bee, hydrolyzed elastin, hydrolyzed collagen, hydrolyzed silk, hydrolyzed keratin, erythritol, capryl glycol, Isoceteth-(3-10, 20, 30) Isolaureth-(3-10, 20, 30) Laneth-(5-50), Laureth-(1-30) Esteareto-(4-20) Trideceth-(5-50), or mixtures thereof.

In one embodiment, the peptide composition for hair treatment may comprise at least one naturally derived cationic polymer selected from the following list: Polyquaternium-10, Polyquaternium-7, Polyquaternium-LLM guar hydroxypropyltrimonium chloride, or mixtures thereof.

In another embodiment, the peptide composition for hair treatment may comprise at least one silicone selected from the following list: amodimethicone, amodimethicone, trideceth-12, cetrimonium mix chloride behenoxi, dimethicone, cetearyl meticona, cetyl dimethicone, cyclomethicone, ciclopentassiloxano, dimethicone, dimethicone copolyol, dimethiconol, hydroxypropyl hydrolyzed wheat protein polysiloxane esteaRoxi dimethicone, stearyl dimethicone, trimetilssililamodimeticona, laurel meticona copolyol, or mixtures thereof.

In yet another embodiment, the peptide composition for hair treatment may comprise at least one organic oil selected from the following list: mineral oil, paraffin, petrolatum.

In one embodiment, the peptide composition for hair treatment may comprise at least one from the following list protein selected from: cocodimónio hydroxypropyl hydrolyzed casein, cocodimónio hydroxypropyl hydrolyzed collagen, cocodimónio hydroxypropyl hydrolyzed keratin, hydroxypropyl cocodimónio rice protein hydrolyzed silk hydroxypropyl cocodimónio hydrolyzed soy hydroxypropyl cocodimónio hydrolyzed hydroxypropyl cocodimónio hydrolyzed wheat protein, hydroxypropyl cocodirmónio silk amino acids, hydrolyzed collagen cocoyl, cocoyl hydrolyzed keratin, hydrolyzed keratin, hydrolyzed oat protein, hydrolyzed silk, hydrolyzed silk protein, hydrolyzed soy protein, hydrolyzed wheat protein, keratin, collagen hydrolyzate potassium cocoyl, TEA-cocoyl hydrolyzed collagen, TEA-cocoyl hydrolyzed soy protein, or mixtures thereof.

In another embodiment, the peptide composition for hair treatment may comprise at least one vitamin selected from the following list: retinol, retinyl palmitate, tocopherol acetate, or mixtures thereof.

In yet another embodiment, the peptide composition for hair treatment may comprise at least one emollient ester selected from the following list: butyl myristate, butyl stearate, C12-15 alkyl benzoate, caprylic triglyceride/capric triglyceride, cetyl octanoate, cetyl stearate, cetearyl stearate, decyl oleate, isostearate dimethyl lauramine, glycerine stearate, glycerine adipate, glyceryl arachidate, glycerin arachidonate, glycerol behenate, glyceryl caprate, glyceryl caprylate, citrate/lactate/linoleate oleate, glycerin, glyceryl cocoate, glyceryl diaraquidato, glycerin dibehenate, glycerin dierucato, glycerin dihidroxiesterato, glyceryl diisopalmitato, glyceryl diisostearate, glyceryl dilaurate, glyceryl dilinoleate, glyceryl dimyristate, glyceryl dioleate, dipalmitate glycerin, glycerin dipalmitoleato, dirricinoleato glycerin, glycerin distearate, erucate glycerin, glycol stearate, stearate of isocetil myristate, isopropyl palmitate, isopropyl, isopropyl stearate, isostearyl stearate, octilpalmitato, octilestearato, propylene glycol dicaprylate/dicaprate, sorbitan benzoate, sorbitan caprylate, sorbitan isostearate, sorbitan laurate, sorbitan tristearate, stearyl stearate, tocopheryl linoleate, or mixtures thereof.

In one embodiment, the peptide composition for hair treatment may comprise at least one alkanolamide selected from the following list: acetamide MEA, cocamide DEA, cocamide MEA, lactamide MEA, lauramide DEA, lauramide DEA, propylene glycol, lauramide MEA, lecitinamida DEA, linoleamide DEA, linoleamide MEA, linoleamide MIPA, myristamide DEA, myristamide MEA, myristamide MIPA, oleamide DEA, oleamide DEA, oleamide MEA, oleamide MIPA, soybean amide DEA, stearamide MEA, and mixtures thereof.

In another embodiment, the peptide composition for hair treatment may comprise at least one amine selected from the following list: dimethylamine behentamidopropil, dimethylamine cocamidopropyl, isoestearamidopropil dimethylamine, lauramidopropyl dimethylamine, miristamidopropil dimethylamine, oleamidopropil dimethylamine, dimethylamine palmitamidopropil, stearamidopropyl dimethylamine or mixtures thereof.

In yet another embodiment, the peptide composition for hair treatment may comprise at least one pH adjusting compound selected from the following list: ascorbic acid, citric acid, sodium hydroxide, triethanolamine, or mixtures thereof. In one embodiment, the peptide composition for hair treatment may comprise at least one selected from the following list salt: calcium chloride, magnesium chloride, magnesium sulfate, potassium chloride, potassium sulfate, sodium chloride, or mixtures thereof.

In another embodiment, the peptide composition for hair treatment may comprise at least one selected aliphatic alcohol from the following list: behenyl alcohol, cetearyl alcohol, cetyl alcohol, isocetyl alcohol, isostearyl alcohol, lauryl alcohol, myristyl alcohol, stearyl, C30-50 alcohols, lanolin alcohol, or mixtures thereof.

In yet another embodiment, the peptide composition for hair treatment may comprise at least one UV filter selected from the following list: benzophenone (2, 3, 4, 5, 6, 7, 8, 9, or 10), benzyl salicylate, benzylidenecamphor sulfonic acid, bornelone, ethyl cinnamate, ethylhexyl methoxycinnamate (octyl methoxycinnamate), octoxynol-40, -20, octyl methoxycinnamate, octyl salicylate, oxybenzone, phenyl ketone, PEG-25 PABA, benzylidene poliacrilamidometil camphor, or mixtures thereof.

In one embodiment, the peptide composition for hair treatment may comprise at least one selected natural oil the following list: coconut oil, jojoba oil, olive oil, palm oil, safflower oil, sesame seed oil, shea butter, sweet almond oil, wheat germ oil, or mixtures thereof.

In another embodiment, the peptide composition for hair treatment may comprise at least one amine oxide selected from the following list: cocamine, lauramine oxide, or mixtures thereof.

In yet another embodiment, the peptide composition for hair treatment may comprise at least one chelator selected from the following list: diisopropyl oxalate, disodium EDTA, disodium EDTA copper, HEDTA, oxalic acid, potassium citrate, sodium oxalate, TEA-EDTA, tetrasodium EDTA, trisodium EDTA, trisodium HEDTA, or mixtures thereof. In one embodiment, the peptide composition for hair treatment may comprise at least one selected fatty acid of the following list: ariquidónico acid, capric acid, coconut fatty acid, lauric acid, linoleic acid, linolenic acid, myristic acid, palmitic acid, pantothenic acid, stearic acid, caproic acid, carboxylic acid Capryleth-(4, 6, 9), isostearic acid, or mixtures thereof.

In another embodiment, the peptide composition for hair treatment may comprise at least one antimicrobial/antibacterial selected from the following list: glyoxal, triclosan, or mixtures thereof.

In yet another embodiment, the peptide composition for hair treatment may comprise at least one PEG-modified materials selected from the following list: PEG-150 in pentaeritirtil tetrastearate, PEG-2 distearate, -3, -4, -6, -8, -12, -20, -32, -50, -150, -175, PEG-10 castor oil, PEG-10 cocamine, PEG-10 cocoate, PEG-10 coconut oil, PEG-10 glyceryl oleate esters, PEG-10 glyceryl stearate, PEG-10 hydrogenated lanolin, PEG-10 hydrogenated tallow amine, thioether isolauril PEG-10, PEG-10 isostearate, lanolate PEG-10, PEG-10 lanolin, PEG-10 laurate, PEG-10 oleate, PEG-10 olive glycerides, PEG-10 laurate, polyglyceryl-2, propylene glycol PEG-10, PEG-10 sorbitan laurate, PEG-10 soya sterol, PEG-10 soyamine, stearamine PEG-10, PEG-10 stearate, PEG-10 chloride stearyl benzonio, PEG-10 tallate, PEG-10 tallow aminopropylamine, PEG-100, PEG-100 castor oil, PEG-100 castor oil hydrogenated Lanolin PEG-100, PEG-100 stearate, PEG-40 hydrogenated castor oil, PEG-60, PEG-55 distearate, propylene glycol, or mixtures thereof.

In one embodiment, the peptide composition for hair treatment may comprise a polymer selected in the following list: carbopol, copolymer dodecanedioic acid/cetearyl alcohol/glycol, hydrogenated C6-14 olefin polymers, hydrogenated ethylene/propylene/styrene: polyacrylic acid, polymethyl methacrylate polymer, polyvinyl acetate, polyvinyl alcohol, PPG, PPG-25-Laureth-25, PPG-5 pentaeritiritil ether, PPG-75-PEG-300-hexylene glycol, polyvinylpyrrolidone, copolymer polyvinylpyrrolidone/vinyl acetate, sodium carbopol, TEA, carbopol, poloxamer (100-407) poloaxamina, poliacrilamidometilpropano sulfonic acid, polyethylene terephthalate, or mixtures thereof.

In another embodiment, the peptide composition for hair treatment may comprise at least one antistatic agent selected from the following list: ethosulfate amidopropyl ethyldimonium, amidopropyl ethyldimonium lactate, cocamidopropyl ethosulfate ethyldimonium, cocamidopropyl lactate ethyldimonium, lauramidopropyl ethosulfate ethyldimonium, lauramidopropyl ethyldimonium lactate, linoleamidopropil ethyldimonium ethosulfate, lactate linoleamidopropil ethyldimonium, miristamidopropil ethyldimonium ethosulfate, lactate miristamidopropil ethyldimonium, oleamidopropil ethyldimonium ethosulfate, lactate ethyldimonium oleamidopropil, stearamidopropil ethyldimonium ethosulfate, stearamidopropil ethyldimonium lactate, or mixtures thereof.

In yet another embodiment, the peptide composition for hair treatment may comprise at least one alcohol selected in the following list: SD-40 alcohol, witch hazel, isopropanol, or mixtures thereof.

In one embodiment, the peptide composition for hair treatment can further comprise fragrances, oils, or mixtures thereof.

In another embodiment, the composition can be used in medicine, veterinary and/or as cosmetics, preferably for treatment by or hair in particular human or animal, particularly for treating scalp disorders, in particular hair irritation, alopecia areata, hair lichen plan, keloid folliculitis neck, trichorrhexis gnarled, tricodistrofia, pill torti, tricorrexis invaginata, monilethrix, the Uncombable hair syndrome.

In another embodiment, the composition may further comprise a coloring agent/dye bound to the N or C terminus of said peptide.

In another embodiment, the composition can be used for coloring hair/fur. Another aspect is the use of the composition described as strengthening hair or the hair or as permanent fastener and/or snails.

Further disclosed in this application shampoo, lotion, serum, cream, conditioner, foam, mouthwash, oil, aerosol or mask comprising the composition presented in this application also.

The present application relates to a composition for hair care comprising in whole or in part, one or more peptide sequences of Aquis Pep1 and Aquis Pep2 for treatment and cosmetics for animal, preferably human hair, chemically pretreated or not. Thus the presence of cysteine in the sequence of the peptides (more than 10%, preferably greater than 15%) in combination with a percentage of hydrophobic amino acids ensures that the peptides can be set in a more durably on hair, improving longer the human hair properties such as elasticity, strength and hydrophobicity.

In the present description, the peptide composition described may be applied to the human hair and in particular to the form of, but not limited to, an aqueous solution or conventional preparation conditioner or shampoo. It may also be in the form of a lotion, foam, aerosol, gel, mask, implementing formulation with or without subsequent rinsing.

The concentration of peptide to be used depends on various characteristics, such as condition of the hair, the origin and the formulation of the hair care product.

It should be understood that the detailed description and specific examples are preferred embodiments of the invention indicators, being provided only for illustrative character, this not being limited to these patent applications.

FIGS. 1, 2 and 3 show the binding affinity of keratin to peptide Aquis 1, 2 and 3.

As shown in the Figures, Peptide Aquis 1 has the most affinity to hair keratin, even higher that KP peptide who showed in previous publications a penetration to the hair cortex, binding to hair keratin and improvement of hair mechanical properties from within the hair. These results show that Aquis Pep 1 can lead to stronger hair by penetrating the hair cortex and binding to hair keratin when applied to the hair in a cosmetic formulation.

The present application describes a composition for hair treatment comprising different peptides, which are based on the structure of keratin and keratin-associated proteins.

The compositions described in this application surprisingly allow the dermo-cosmetic treatment of the animal, including human hair, chemically pre-treated or not. The composition described in the present invention by certain specific peptides allows repair damage keratin fibers, this can be explained by the high binding capacity of the peptides to keratin, particularly through disulfide bonds.

The compositions described improved properties and characteristics of the/hair, such as elasticity, strength and appearance, repairing any damage hair/fur.

The identified peptides are peptide sequences that bind to a certain affinity to the hair. The peptides used in this invention are composed of 11 and 12 amino acids, and consist of a minimum of 2 and a maximum of 3 cysteines.

The peptide composition for hair treatment described increased resistance due to the presence of a cysteine-rich peptide which leads to the penetration of hair/fur, hair strengthening the resistance/even after the washes.

Each peptide may be used together or separately as well as in all or part of the peptide sequence, the hair cosmetic composition. Each peptide sequence containing amino acid residues containing sulfur, specifically cysteine that interact with the hair and allows the formation of intermolecular cross-linking, stabilizing the keratin fiber.

The peptide composition described uses a high content of cysteine in order to enhance their properties, such as improved elasticity and strength, reduce potential damage by, improvement and/or alteration of its characteristics. From the point of view of interactions with the keratinous fibers, the amino acids are cysteine residues 18% to 25% of the total amino acids of the peptide sequence. Additionally, from the viewpoint of the size of peptide sequence number is preferably 11 to 12.

The peptides can be used alone or in combination of the two at various ratio. The concentration of peptide to be used depends on various characteristics, such as condition of the hair, the origin and the formulation of the hair care product. Hair composition of the contents of the present invention is exemplarily 1-between 0.001% (w/w) by weight.

The peptides of this invention may be prepared using conventional peptide synthesis methods well known in the art as well as biotechnology technique such as for example but not limited to microorganisms engineering and fermentation.

In addition many companies provide custom peptide synthesis services.

The sequences of the peptides are listed in Table 1.

As an example of the animal, tresses were used virgin human hair. The term virgin hair is applied to all of the hair that has never been the subject or at least 10 years without making any chemical treatment. human hair samples are commercially available, for example in companies already above in different in various types of hair such as African, Caucasian and Asian. Optionally, the hair samples can be treated for example using hydrogen peroxide to decolorize hair techniques necessary for example to dye the hair.

In the present invention, the peptides may be applied to the human hair and in particular in the form of, but not limited to, aqueous or conventional preparation conditioner or shampoo. It may also be in the form of a lotion, foam, aerosol, gel, mask, implementing formulation with or without subsequent rinsing.

This application can be prepared by coupling the peptide with an agent such preparations either directly or via an optional spacer.

This coupling interaction can be carried out by covalent or non-covalent bonds such as hydrogen bonds, electrostatic interactions, hydrophobic interactions or van der Waals interactions. The optional spacer serves to separate the preparation of the peptide agent, assuring that the agent will not interfere with the binding of the peptide to the hair.

The present invention can be understood more clearly and accurately by reading the following examples which are preferred embodiments indicators of the invention and are provided for illustration in greater detail of the present invention without providing any limitation not being this patent limited to such applications.

APPLICATION EXAMPLES

The examples that are within the scope of the claims represent different embodiments of the invention; all the other examples are comparative examples.

Example 1: Affinity Binding

Affinity of Aquis peptides with natural hair keratin were tested. Peptides and Keratin sequences tested are shown in FIG. 2. A third peptide was also tested with the sequence GGVCGPSPPCITT known as KP developed by Khairpep as a control. KP has been shown in previous patent and publications to penetrate the hair shaft, bind to keratin and improve hair mechanical properties.

Various concentrations of Keratin dissolved in water were manually printed onto the bare gold coated (thickness 47 nm) PlexArray Nanocapture Sensor Chip (Plexera Bioscience, Seattle, Wash., US) at 40% humidity. Each concentration was printed in replicate, and each spot contained 0.2 uL of Myosin solution. The chip was incubated in 80% humidity at 4° C. for overnight, and rinsed with 10×PBST for 10 min, 1×PBST for 10 min, and deionized water twice for 10 min. The chip was then blocked with 5% (w/v) non-fat milk in water overnight, and washed with 10×PBST for 10 min, 1×PBST for 10 min, and deionized water twice for 10 min before being dried under a stream of nitrogen prior to use. SPRi measurements were performed with PlexAray HT (Plexera Bioscience, Seattle, Wash., US). Collimated light (660 nm) passes through the coupling prism, reflects off the SPR-active gold surface, and is received the CCD camera. Buffers and samples were injected by a non-pulsatile piston pump into the 30 uL flowcell that was mounted on the coupling prim. Each measurement cycle contained four steps: washing with PBST running buffer at a constant rate of 2 uL/s to obtain a stable baseline, sample injection at 5 uL/s for binding, surface washing with PBST at 2 uL/s for 300 s, and regeneration with 0.5% (v/v) H3PO4 at 2 uL/s for 300 s. All the measurements were performed at 4° C. The signal changes after binding and washing (in AU) are recorded as the assay value. Selected protein-grafted regions in the SPR images were analyzed, and the average reflectivity variations of the chosen areas were plotted as a function of time. Real-time binding signals were recorded and analyzed by Data Analysis Module (DAM, Plexera Bioscience, Seattle, Wash., US). Kinetic analysis was performed using BIAevaluation 4.1 software (Biacore, Inc.).

Table 2 shows the difference sequences, peptides properties and summary of results. FIGS. 1 to 3 show the binding affinity to keratin for each peptide tested. The lower the KD value is, the more affinity the peptide has to hair keratin.

TABLE 21

| Sequence | Name AA |
|---|---|
| FCGFPSCSTSG<br>SEQ ID NO 1<br>LENGTH: 11<br>TYPE: PRT<br>ORGANISM: Artificial Sequence<br>FEATURE:<br>OTHER INFORMATION: PEPTIDE<br>AA: 11<br>MW (da): 1092.2<br>pI: 5.51<br>Cys%: 18.2<br>Hydrophob. %: 27<br>KD Value in M(10)$^{-7}$: 3.65<br>Affinity Ranking: 1<br>SEQUENCE: 1<br>Phe Cys Gly Phe Pro Ser Cys Ser Thr Ser Gly<br>1             5                  10 | Aquis Pep1 |
| CTPPSCCQLHHA<br>SEQ ID NO 2<br>LENGTH: 12<br>TYPE: PRT<br>ORGANISM: Artificial Sequence<br>FEATURE:<br>OTHER INFORMATION: PEPTIDE<br>AA: 12<br>MW (da): 1296.49<br>pI: 6.89<br>Cys %:25<br>Hydrophob. %: 33<br>KD Value in M (10)$^{-7}$: 25<br>Affinity Ranking: 3<br>SEQUENCE: 2<br>Cys Thr Pro Pro Ser Cys Cys Gln Leu His His Ala<br>1             5                  10 | Aquis Pep 2 |
| GGVCPSPPCITT<br>SEQ ID NO 3<br>LENGTH: 10<br>TYPE: PRT<br>ORGANISM: Artificial Sequence<br>FEATURE:<br>OTHER INFORMATION: PEPTIDE<br>AA: 13<br>MW (da): 1188<br>pI: 5.51<br>Cys %: 15<br>Hydrophob. %: 38<br>KD Value In M (10)$^{-7}$: 8.14<br>Affinity Ranking: 2<br>SEQUENCE: 3<br>Ala Ser Cys Arg Pro Ser Tyr Cys Gly<br>1             5                  10 | KP |
| ASCCRPSYCG<br>SEQ ID NO 4<br>LENGTH: 10<br>TYPE: PRT<br>ORGANISM: Artificial Sequence<br>FEATURE:<br>OTHER INFORMATION: PEPTIDE<br>AA: 202<br>MW (da): 21069.03<br>pI: 6.58<br>Cys %: 8.40<br>Hydrophob. %: 33<br>PALYMITOYL IS ATTACHED TOTHIS POSITION<br>SEQUENCE: 4<br>Ala Ser Cys Cys Arg Pro Tyr Cys Gly<br>1             5                  10 | Hair Keratin<br>KRTHB1 Basic |

Although a preferred embodiment of the invention has been disclosed here for the purposes of illustration, it should be understood that various changes, modifications and substitutions may be incorporated in the embodiment without departing from the spirit of the invention, which is defined by the claims which follow.

What is claimed is:

1. A peptide composition for treating hair, comprising:
   at least one peptide sequence consisting essentially of AquisPep1 or AquisPep2; and
   at least one excipient suitable for dermatological use;
   wherein the peptide composition is a lotion or cream.

2. The composition according to claim 1, wherein the at east one excipient is selected from: anionic surfactant, amphoteric surfactant, cationic surfactant, nonionic surfactant, emulsifier, preservative, thickener, naturally derived polymer, naturally derived humectant, naturally derived cationic polymer, silicone, protein, vitamin, emollient ester alkanolamide, amino, pH adjusting compound, a salt, an aliphatic alcohol, UV oil, amine oxide, chelate, fatty acid, PEG material, polymer, antistatic agent, alcohol, or combinations thereof.

3. The composition according to claim 1, wherein the peptide sequence is present at a concentration from 0.001% to 20% (w/w).

4. The composition according to claim 1, wherein the at least one excipient is selected from surfactants, emulsifiers, preservatives, thickeners, organic polymers, humectants, silicones, oils, fragrances, vitamins, buffers, antimicrobial agents, antibacterial agents, disinfectants, or combinations thereof.

5. The composition according to claim 1, further comprising fragrances, oils, or mixtures thereof.

6. The composition according to claim 1, further comprising a coloring agent dye bound to the N or C terminus of the peptide sequence.

7. A peptide composition for treating hair, comprising:
   at least one peptide sequence consisting of AquisPep1 or AquisPep2;

at least one surfactant selected from an anionic surfactant, an amphoteric surfactant, a cationic surfactant, a nonionic surfactant, and combinations thereof; and a coloring agent/dye bound to the N or C terminus of the peptide sequence.

\* \* \* \* \*